United States Patent [19]

Thornton et al.

[11] Patent Number: 4,830,968
[45] Date of Patent: May 16, 1989

[54] WINE MAKING INOCULANTS AND RELATED MEANS AND METHODS

[76] Inventors: Roy J. Thornton, 30 Rangitira Avenue, Palmerston North, New Zealand; Susan B. Rodriguez, 15 Reed Rd. #174, Geneva, N.Y. 14456

[21] Appl. No.: 928,432

[22] Filed: Nov. 10, 1986

[30] Foreign Application Priority Data

Nov. 13, 1985 [NZ] New Zealand .......................... 214177

[51] Int. Cl.$^4$ ........................ C12N 1/16; C12N 15/00; C12R 1/645; C12G 1/00
[52] U.S. Cl. .................................. 435/255; 435/172.1; 435/911; 426/15
[58] Field of Search ...................... 435/911, 161, 172.1, 435/256, 255; 426/15

[56] References Cited

PUBLICATIONS

Totsuka et al., Hakko Kogaku Kaishi, vol. 59(3) pp. 231–237 (Abstract) 1981.
Sipizki et al., Journal of General Microbiology, vol. 128, pp. 1989–2000, (1982).
Gentner, Norman C., (1981) Chemical Abstract, vol. 94(23); Abstract 186142s.
CA 96:33309T.
Radler, *Experientia*, 42, 884 (1986).
Rankine, *J. Sci. Fd. Agric.*, 17, 312 (1966).

*Primary Examiner*—Elizabeth C. Weimar
*Attorney, Agent, or Firm*—Armstrong, Nikaido, Marmelstein & Kubovcik

[57] ABSTRACT

The invention provides a method of wine making which includes the step of inoculating the grape juice with a strain of *Schizosaccharomyces malidevorans* which is capable of at least substantially completely utilizing L-malic acid without substantial utilization of glucose under wine-making conditions. Strains of *Schizosaccharomyces malidevorans* having the above capability and a screen for identifying such strains are other aspects of the invention.

5 Claims, No Drawings

WINE MAKING INOCULANTS AND RELATED MEANS AND METHODS

The present invention relates to improvement in and/or relating to wine-making, novel microorganisms useful in wine-making, screening techniques and plates, etc. enabling identification and separation of microorganisms useful in wine-making, organisms thus separated and their use in wine-making and related means and methods.

There are two major reasons for carrying out a malo-lactic fermentation on wines. These are deacidification and microbial stability.

Grapes grown in cool climates, such as New Zealand, make wines of unacceptably high acidity. This problem does not exist in warmer climates, such as Australia, because the grape metabolizes much of the acid and the high sugar level can balance the high acid.

Wine-makers have a choice of biological or chemical deacidification of the wine or juice. They seem to prefer the biological method which involves "encouraging" the growth of lactic acid bacteria in their wines. These bacteria deacidify the wine by converting malic acid to the less strong lactic acid. This conversion is called the malolactic fermentation (MLF). Since these bacteria (species of Leuconostoc, Lactobacillus and Pediococcus) are found on grapes and can become part of the winery microflora, some wine-makers depend upon the spontaneous growth of these bacteria in the wine. Other winemakers purchase cultures of these bacteria with which to inoculate their wines. These bacteria are much more difficult to grow than yeast - temperatures below 60° F. are inhibitory for growth; a sulfur dioxide (SO2) concentration greater than 20 ppm free SO2 could kill the bacteria; a wine which has completed alcoholic fermentation may be too depleted in nutrients to support growth, and there is always the possibility of viral (bacteriophage) attack.

Notwithstanding the sensitivity of ML bacteria to the various factors mentioned previously, most wines can support their growth.

This growth is usually accompanied by the production of carbon dioxide, and this is an obvious problem in packaged wine resulting in "fizzy" bottles and packets of bag-in-the-box still wine. Wines which do *not* need deacidification are often put through MLF to "stabilise" them, i.e. deplete the malic acid so that the risk of growth of malo-lactic bacteria in the packaged wine is avoided.

Regardless of whether the wine-maker depends upon spontaneous growth of ML bacteria or inoculates with commercially available frozen or freeze-dried cultures, the MLF is a difficult and time-consuming process.

The MLF usually follows the alcoholic fermentation conducted by yeast, and depending upon local conditions, may take from three to twelve weeks to complete. During this period the wine may actually deteriorate in quality since it is still in contact with the yeast cells which are beginning to break down and release cell product into the wine.

Many researchers have attempted to simplify this complex biological deacidification procedure. Some have isolated strains of malolactic (ML) bacteria which are more cold tolerant or more SO2 tolerant or go through MLF reliably (Beelman, R.B., A. Gavin II, and R.M. Keen, "A new strain of *Leuconostoc oenos* for induced malo-lactic fermentation in eastern wines", Am. J. Enol. Vitic. 28, (1977) 159-165.; Silver, J., and T. Leighton, "Control of malo-lactic fermentation in wine: Isolation and characterization of a new malo-lactic organism", Am. J. Enol. Vitic. 32 (1981) 64–72.) Others, using the knowledge that yeasts are easier to grow than ML bacteria, have tried to use yeasts which degrade malic acid, e.g. Schizosaccharomyces (Snow, P.G., and J.F. Gallander, "Deacidification of white table wines through partial fermentation with *Schizosaccharomyces pombe*", Am. J. Enol. Vitic. 30 (1979) 45–48) or have attempted to clone the ML bacterial gene into a wine yeast (Williams, S.A., R.A. Hodges, T.L. Strike, R. Snow and R.E. Kunkee, "Cloning the gene for the malo-lactic fermentation of wine from *Lactobacillus delbrueckii* in *Escherichia coli* and yeasts, Appl. Envir. Microbiol. 47 (1984), 288–293). The former method has not been successful because of the variable degree of deacidification (probably due to the fact that Schizosaccharomyces is overgrown by the yeast used for the alcoholic fermentation) and the off-flavours produced. The latter attempt did not work because the genetically engineered yeast did not degrade malic acid to a significant extent.

*Technology of Wine Making* (4th Edition, Amerine, Berg, Kunkee, Ough, Singleton, Webb, A.V. Publishing Co., Inc., Westport, Connecticut, USA, 1980, pg 173) identifies Schizosaccharomyces as the name given by Lindner about 1893 to a strain of genus of yeasts known as fission yeasts. Such yeasts multiply in the same manner as bacteria by formation of a transverse wall or septum in the cell and the splitting of the two cells into two new cells along the line of septum. The yeast described by Lindner was isolated from African beer. Lodder and Kreger-Van (*The Yeasts: A Taxonomic Study*, Ed. 1970, North Holland Publishing Company, Netherlands) states that the genus contains four species namely *Schizosaccharomyces japonicus, Schizosaccharomyces malidevorans, Schizosaccharomyces pombe* and *Schizosaccharomyces octosporus*. The previously referred to articles deal to some extent with the acidification attempts using certain of these species, particularly *Schizosaccharomyces pombe*.

In an article entitled "Decomposition of L-malic acid by wine yeasts" (Journal of Science and Food Agriculture 17 (1966) 312-316) B.C. Rankine discusses the usefulness of a certain strain of *Schizosaccharomyces malidevorans* in decomposing L-malic acid in grape juice. The strain referred to in the article as No. 442 (Rankine) was the only one that gave complete utilisation of L-malic acid and showed no pH dependence. Mutation with ultraviolet irradiation in an attempt to obtain a mutant which would not produce hydrogen sulphide whilst retaining the property of L-malic acid decomposition was unsuccessful.

The strain *Schizosaccharomyces malidevorans* 442, supplied by Dr B. Rankine of Roseworthy Agricultural College of Advanced Education, South Australia, was used in the mutagenesis which led to the novel strain which constitutes one aspect of the present invention. A similar if not identical organism to that of Dr Rankine has been deposited at Centraalbureau voor Schimmelcultures as CBS 5557, and is believed to be the same as that deposited with the American Type Culture Collection (ATCC 46954) by Dr E. Johansen, Microbiology Research Group, Pretoria, South Africa. The microscopic and colonia morphology of the parent strain obtained from Dr Rankine, that of CBS 5557 and indeed that of the mutated strain (whose microscopic and colonial morphology is not distinguishable from that of the parent strain) are as detailed in the entry for *Schizosaccharomyces malidevorans* in *Yeasts: characteristics and identification,* Barnett, J.A., Payne, R.W., Yarrow, D. (Cambridge University Press, 1983). The morphology is as follows:

DESCRIPTION

Cream or tan colonies; vegetative reproduction by splitting; no filaments; evanescent asci, containing 1 to 4 smooth, oval or round ascospores.

which constitute another aspect of the present invention.

The strain most favoured at present is the mutant strain Rodriguez-Thornton #11 deposited as ATCC 20771.

The physiology of Rodriguez-Thornton strain #11 differs from that of the parent strain supplied by Rankine even though the microscopic and colonial morphology is the same.

Strain #11 can grow aerobically and anaerobically on a medium which contains both malic acid and glucose

| Fermentation | | | | | |
|---|---|---|---|---|---|
| 01 D-Glucose | + | 05 Sucrose | + | 09 Cellobiose | − |
| 02 D-Galactose | − | 06 α,α-Trehalose | − | 10 Melezitose | − |
| 03 Maltose | − | 07 Melibiose | − | 11 Raffinose | + |
| | | | | 12 Inulin | − |
| 04 Meα-D-glucoside | − | 08 Lactose | − | 13 Starch | − |
| Growth | | | | | |
| 14 D-Galactose | − | 36 Erythritol | − | 50 Cadavarine | + |
| 15 L-Sorbose | − | 37 Ribitol | − | 59 Creatine | − |
| 16 D-Glucosamine | − | 38 Xylitol | − | 60 Creatinine | − |
| 17 D-Ribose | − | 39 L-Arabinitol | − | 61 w/o Vitamins | − |
| 18 D-Xylose | − | 40 D-Glucitol | − | 62 w/o myo-Inositol | − |
| 19 L-Arabinose | − | 41 D-Mannitol | − | 63 w/o Pantothenate | D− |
| 20 D-Arabinose | − | 42 Galactitol | − | 64 w/o Biotin | − |
| 21 L-Rhamnose | − | 43 myo-Inositol | − | 65 w/o Thiamin | + |
| 22 Sucrose | + | 44 D-Glucono-1,5 lactone | + | 66 w/o Biotin & Thiamin | − |
| 23 Maltose | − | | | | |
| 24 α,α-Trehalose | − | 45 2-Keto-D-gluconate | + | 67 w/o Pyridoxine | + |
| 25 Me—D-glucoside | − | | | 68 w/o Niacin | − |
| | | 46 5-Keto-D-gluconate | − | 69 w/o Folic acid | + |
| 26 Cellobiose | − | | | 70 w/o PABA | + |
| 27 Salicin | − | 47 D-Gluconate | D | 71 at 25° C. | + |
| 28 Arbutin | − | 48 D-Glucuronate | − | 72 at 30° C. | + |
| 29 Melibiose | − | 49 DL-Lactate | − | 73 at 35° C. | + |
| 30 Lactose | − | 50 Succinate | − | 74 at 37° C. | + |
| 31 Raffinose | + | 51 Citrate | − | 75 at 42° C. | − |
| 32 Melezitose | − | 52 Methanol | − | 76 0.01% Cycloheximide | D |
| 33 Inulin | D | 53 Ethanol | − | 77 0.1% Cycloheximide | − |
| 34 Starch | − | 54 Nitrate | − | 78 50% D-Glucose | + |
| 35 Glycerol | − | 55 Nitrate | − | 79 60% D-Glucose | + |
| | | 56 Ethylamine | − | | |
| | | 57 L-Lysine | W | | |
| Additional Characteristics | | | | | |
| 80 Starch Formation | − | | | 82 Urea hydrolysis | + |
| 81 Acetic acid production | − | | | 83 Dizaonium blue reaction | − |

+ = a score of 2+ or 3+ using Wickerham's scale within 7 days.
D = same score after a delay of 14 or 21 days.
− = failure to grow
W = growth tests with nitrogen sources where done using auxanograms which were examined after 4 days of incubation: clearly visible, dense zone of growth is "+", a barely discernible zone is "W".

Other descriptions can be found in Lodder, J., and Kreger-Van, R.J. NJM (EDS) *The Yeasts: A Taxonomic Study,* 2nd Ed., 1970, North Holland Publishing Company, Netherlands.

It is an object of the present invention to provide a method and means of making wine which goes some way towards overcoming the above disadvantages or to at least provide the public with a useful choice.

In one aspect, the present invention consists in a strain of *Schizosaccharomyces malidevorans* or a mutant thereof which is capable of completely or substantially completely utilising L-malic acid without substantial utilisation of glucose under wine making conditions.

Preferably the strain is in a substantially pure form.

Preferably the strain is a mutant of *Schizosaccharomyces malidevorans* 442 (CBS 5557).

Although other methods such as chemical mutagenesis may be used, the mutant strain is conveniently obtained by exposure of the abovementioned strain *Schizosaccharomyces malidevorans* 442 to UV irradiation.

The separation of the mutant strain is preferably carried out using a screen plate and related procedures (or fructose), a nitrogen source and yeast vitamins. This distinguishes strain #11 from its parent since the latter can grow aerobically and anaerobically with glucose as sole carbon source whereas strain #11 requires the presence of both glucose and malic acid for growth. (The ability of strain #11 to ferment and/or assimilate other carbon sources has not been determined, so a complete comparison with the parent strain cannot be made.)

The genetic characterisation of the mutations(s) which causes strain #11 to differ from the parent strain is in progress. It is intended to determine whether (a) the different phenotype is due to mutation in one or more genes and (b) locate the same on the chromosome map of *Schizosaccharomyces malidevorans.*

The nature of the *Schizosaccharomyces malidevorans* mutant that we have isolated is such that it will provide the wine maker with a viable alternative to the tricky and time-consuming MLF. The reasons for this assertion include:

1. The mutant does utilise far less glucose than the parent strain, although it does require the presence of glucose in order to utilise malic acid. This characteristic means that many of the metabolic pathways are either inactive or have greatly reduced activity and, in doing so, has reduced the number of compounds capable of producing off-flavours.

2. The mutant utilises malic acid at a faster rate than does the wild type *Schizosaccharomyces malidevorans* (within 36 hours at 25° C. in pure culture).

3. The viability of the mutant far exceeds that of the wild type. Thus, the possibility of overgrowth by culture yeast before it has utilised all of the malic acid is much reduced.

4. As the mutant is a yeast there is a much better probability of successfully preparing freeze-dried cultures for inoculation than is the case with ML bacteria.

The present invention also consists in a method of wine-making which includes as a step the utilisation of malic acid by a strain of *Schizosaccharomyces malidevorans* in accordance with the present invention (i.e. a strain of *Schizosaccharomyces malidevorans* or a mutant thereof which is capable of completely or substantially completely utilising malic acid without substantial utilisation of glucose). Preferably the mutant is Rogriguez-Thornton #11 or any other mutant strain isolated using a screening and isolation procedure in accordance with the present invention.

The current process of making red wine (and some white wines) involves an alcoholic fermentation of grape juice by wine yeast followed by a secondary fermentation carried out by the bacterium *Leuconostoc oenos*, which is used to inoculate the wine and in the course of 6 weeks converts malic acid to lactic acid (the malo-lactic or MLF fermentation). The whole wine-making process may take 8-10 weeks and the MLF is an unpredictable process during which wine spoilage may occur.

Using the yeast strains of the present invention two possible procedures of wine-making are envisaged.

1. Inoculation of grape juice with the mutant followed by incubation at 25° C. for 24-36 hours. In this time all the malic acid would be utilised and the grape juice could then be inoculated with a culture yeast which would carry out the alcoholic fermentation in 10-20 days.

2. Simultaneous inoculation of the grape juice with the mutant and the culture yeast so that malic acid utilisation and alcoholic fermentation proceed together.

It can be seen from the foregoing that it should be possible using the procedures and yeasts of the present invention to carry out the whole double fermentation in approximately 3 weeks compared with 8-10 weeks and this added to the safety factors involved would have obvious cost benefits to wine makers.

In another aspect the present invention consists in a screen for identifying species of yeast having effective malic acid utilisation comprising an inert matrix, L-malic acid, glucose at a concentration of greater than 10% by weight, a source or sources of nitrogen and vitamins and a pH indicator having a gradual colour change over the pH range of about 3 to about 6.5.

The preferred indicator is bromocresol green indicator although other indicators may also be used.

It is further preferred that the glucose content is greater than 15% by weight, and that the inert matrix is agar.

The procedure by which the preferred form of screen plate is prepared will now be described.

To one liter of agar medium, add
6.7 g Difco Yeast Nitrogen Base (w/o amino acids)
150 g D-glucose
10 g L-malic acid
2.2 ml of a 1% aqueous solution of bromocresol green indicator
500 ml distilled water;

Adjust pH to 3.8 using 3N potassium hydroxide.

In a separate flask, mix 20 g agar and 500 ml distilled water. Autoclave both flasks for 15 minutes at 121° C. (15 psi). Cool both flasks to 50° C., mix the contents together and dispense in 20 ml aliquots into sterile petri dishes. The resulting medium is green.

Colour formation of colonies after 7 days incubation at 30° C. by yeasts utilising different amounts of malic acid in the presence of 10% glucose is as follows:

| Dark blue-green or turquoise | 90% malic acid utilisation | *Schizosaccharomyces malidevorans* |
|---|---|---|
| Dark olive-green | 10-40% malic acid utilisation | *Schizosaccharomyces cerevisiae* |
| Pale green | 80% malic acid utilisation | *Zygosaccharomyces bailii* |
| Light green | 60% malic acid utilisation | *Pachysolen tannophilus* |
| Dark olive-green | 10% malic acid utilisation | *Pichia stipitis* |

Using the screen plate *without glucose* gave the following colours after 3 days incubation at 30° C.

| Light blue | 100% malic acid utilisation | *Pachysolen tannophilus* |
|---|---|---|
| Bright blue | 100% malic acid utilisation | *Pichia stipitis* |

All five yeasts incubated on the screen plate medium *without malic acid* gave a yellow colour.

It is to be noted that a screen plate in accordance with the present invention has a range of colour changes over the pH range from 3 to 6.5 which is found favourable for identifying good malic acid utilisation with little glucose utilisation.

Using a screen plate in accordance with the present invention strains #11, #34 and #36 Rodriguez-Thornton were isolated. Strain #11 which is the most favoured has been deposited at the American Type Culture Collection as ATCC 20771. The less preferred strains #34 and #36 have not as yet been deposited at ATCC.

In steps prior to the use of the screen plate a centrifuged and washed culture of *Schizosaccharomyces malidevorans* #442 Rankine was resuspended in sterile water and exposed to ultraviolet (UV) irradiation. The irradiated suspension was diluted in sterile water and aliquots spread onto the screenplates. Sixteen light coloured colonies, including strain #11, were subcultured from the screen plates after 5 days incubation at 30° C. Four more light-coloured clones including strains #34 and #36 were subcultured from the screen plates after a further 24 hours incubation. The remaining light coloured subcultures gave colonies that ranged from light green to turquoise in color.

The parent strain *Schizosaccharomyces malidevorans* #442 and mutant strains #11, #34 and #36 on the screen plate resulted in blue-green or turquoise colonies (parent) and bright blue colonies (#11, #34 and #36) when incubated on the screen plate at 30° C. for 5 days.

It is believed that repeat mutation of *Schizaccharomyces malidevorans* #442 Rankine or closely similar species such as that deposited at ATCC 46954 together with the use of the screen plate of the invention will result frequently in a mutant strain having substantially the characteristics of Rodriguez-Thornton strain #11 being isolated. Such characteristics are readily recognized on the screen.

On the basis of the foregoing, therefore, it can be seen that by virtue of the use of the Rodriguez screen plate (which forms part of the present invention) novel strains mutated from parent *Schizosaccharomyces malidevorans* can be derived which are complete or at worst substantially complete utilizers of L-malic acid and which do not substantially use glucose even when it is present (which, of course, is the case with the Rodriguez screen plate). With such isolated species (e.g. Rodriguez-Thornton #11 strain and to a lesser extent strains #34 and #36) modified wine-making procedures in accordance with the present invention are possible. Persons skilled in the wine-making business will appreciate how modified yeasts in accordance with the present invention can be marketed for such grape fermentation.

What is claimed is:

1. A mutant of strain *Schizosaccharomyces malidevorans* #442 (CBS 5557), which mutant requires the presence of both (a) L-malic acid and (b) glucose or fructose for growth, and which is capable of completely utilizing L-malic acid when grown on a matrix comprising L-malic acid, glucose at concentration of greater than 10% by weight, a nitrogen source, vitamins and a pH indicator having gradual color change over the pH range of about 3 to about 6.5.

2. A mutant as claimed in claim 1 which has been obtained by exposure of *Schizosaccharomyces malidevorans* #442 to ultraviolet irradiation and identification and selection on a screen plate.

3. A mutant as claimed in claim 1, wherein the mutant is *Schizosaccharomyces malidevorans* Rodriguez-Thornton #11 (ATCC 20771).

4. An inoculant for inoculating grape juice in the production of wine, comprising a strain of Schizosaccharomyces malidevorans Rodriguez-Thornton #11 (ATCC 20771) and a non-toxic aqueous carrier.

5. An inoculant as claimed in claim 4 in a storage stable form.

* * * * *